Figure 1:
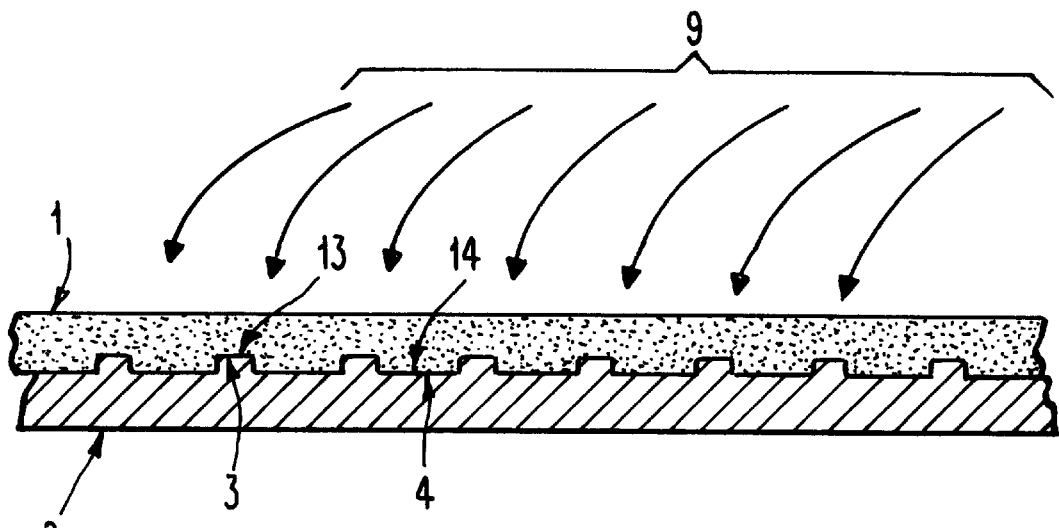
Figure 2:
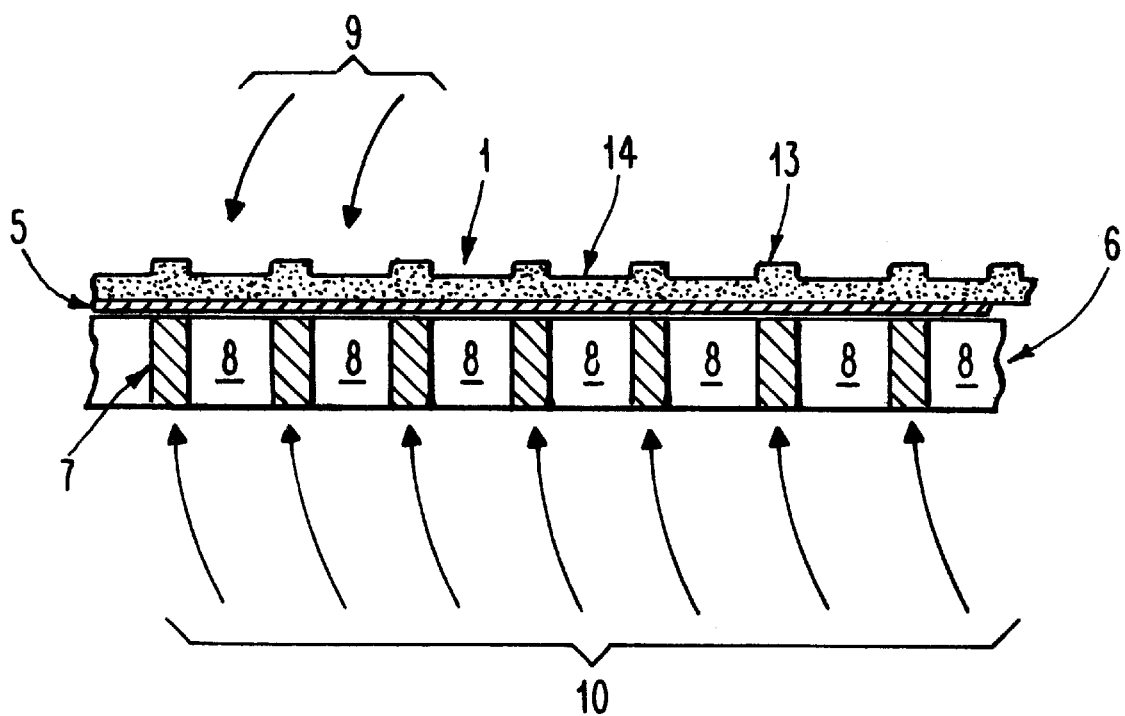

United States Patent [19]
Ludwig

[11] Patent Number: 6,106,930
[45] Date of Patent: *Aug. 22, 2000

[54] PREPARATION CONSISTING OF A SURFACE-ADHERING, FILM-LIKE OR WAFER-LIKE ADMINISTRATION FORM

[75] Inventor: Karin Ludwig, Datzeroth, Germany

[73] Assignee: Isis Pharmaceuticals Inc., Carlsbad, Calif.

[ * ] Notice: This patent is subject to a terminal disclaimer.

[21] Appl. No.: 09/297,698

[22] PCT Filed: Nov. 4, 1997

[86] PCT No.: PCT/EP97/06082

§ 371 Date: May 5, 1999

§ 102(e) Date: May 5, 1999

[87] PCT Pub. No.: WO98/20859

PCT Pub. Date: May 22, 1998

[30] Foreign Application Priority Data

Nov. 13, 1996 [DE] Germany .................. 196 46 836

[51] Int. Cl.[7] .................. B32B 3/00; A61F 13/00
[52] U.S. Cl. .................. 428/156; 428/187; 424/443; 206/534; 264/509; D24/100
[58] Field of Search .................. 428/156, 172, 428/178, 187, 195; 206/528, 534, 538, 828; 424/443, 467; 264/132, 241, 500, 509; D24/100

[56] References Cited

U.S. PATENT DOCUMENTS

| | | | |
|---|---|---|---|
| 4,456,639 | 6/1984 | Drower et al. | 428/13 |
| 4,717,615 | 1/1988 | Reinhart | 428/161 |
| 4,895,257 | 1/1990 | Winslow | 206/534 |
| 4,945,215 | 7/1990 | Fukushima et al. | 235/457 |
| 4,995,408 | 2/1991 | Wallschlaeger | 206/823 |

FOREIGN PATENT DOCUMENTS

| | | |
|---|---|---|
| 0 398 229 A2 | 5/1990 | European Pat. Off. . |
| 002055483 | 8/1994 | WIPO . |
| WO 95/09608 | 4/1995 | WIPO . |

*Primary Examiner*—Donald Loney
*Attorney, Agent, or Firm*—Law Offices of Jane Massey Licata

[57] ABSTRACT

A preparation consisting of a sheet-like, film-like or wafer-like administration form with a coding in the form of characters and/or graphic symbols or patterns for identifying the substances affecting flavor or odor and/or the therapeutic or curative substances which can be released therefrom during use is characterized in that the coding is formed by surface areas of differing thickness.

16 Claims, 1 Drawing Sheet

PREPARATION CONSISTING OF A SURFACE-ADHERING, FILM-LIKE OR WAFER-LIKE ADMINISTRATION FORM

DESCRIPTION

The invention relates to a preparation, consisting of a sheet-like, film-like or wafer-like administration form with a coding in the form of characters and/or graphic symbols or patterns for identifying the substances affecting flavour or odour and/or the therapeutic or curative substances which can be released therefrom during use.

Manufacturers of pharmaceutical products are increasingly obliged to identify not only the primary packaging, but also the product itself. This especially applies to medicaments in an administration form aimed at controlling the release of active substance.

In the prior art, medicaments in the form of pills, tablets and foil-like or film-like products are usually coded in an operation which is additional to the actual manufacture, by printing or punching of special characters or patterns. In addition to the outlay necessitated by this, with correspondingly increased production costs, the introduction of a printing medium, a printing ink, in the printing process, for example, is not uncontroversial, because at least in some cases this creates or unnecessarily increases the risk of allergization.

The object on which the invention is based is to make available, for a preparation of the generic type specified in the preamble, a coding in the form of characters and/or graphic symbols or patterns which avoids the abovementioned disadvantages, in particular the application of a foreign substance such as printing ink, and which consequently avoids the risk of allergization and reduces the corresponding outlay for a coding subordinate to production.

The object is successfully achieved according to the invention, in a preparation of the type mentioned in the preamble of claim 1, by virtue of the fact that the coding is formed by surface areas of differing thickness.

By forming surface areas of differing thickness for the purpose of coding, the application of a logo by printing with food colourings, and the disadvantages described in relation to this, are avoided. Instead, according to the invention, by means of patterned differences in the layer thickness of the film-like or wafer-like administration form, a logo visible to the eye is created in the surface area of the preparation, this logo roughly corresponding in its effect to a so-called watermark in paper-like dispersions. The invention accordingly represents an advantageous alternative to the application of product markings by printing with foreign substances. Although the formation of "watermarks" when drying dispersions on structured supports is likewise based on the formation of thickness variations of the sheet-like paper dispersions, it has never previously been proposed to use this type of identification in connection with film-like, paper-like or wafer-like administration forms for therapeutic or curative substances.

In one embodiment of the preparation, the areas of differing thickness are formed under the production conditions while avoiding different density or compression.

In a further embodiment of the preparation, the areas of differing thickness have a different density (compression).

The method according to the invention for producing the preparation involves the symbols or patterns of the coding being introduced by means of an irreversible deformation in the plastically deformable state.

One method according to the invention for producing the preparation involves the symbols or patterns of the coding being formed in the course of production without the action of pressure (compression).

A further method according to the invention for producing the preparation involves the symbols or patterns of the coding being applied under the action of pressure (compression).

In one embodiment, the thickness differences are produced by coating of a support which has a sequence of elevations and/or depressions corresponding to the coding. Such elevations and depressions can be arranged, for example, on a support similar to a pressure plate by grinding or etching.

In a further proposal according to the invention, the thickness differences can be produced by subjecting the preparation to local temperature differences during drying.

In a further method according to the invention for producing the preparation, the thickness differences are introduced continuously, for example with a structured embossing roller, or intermittently, for example with a stamp.

The production of coded sheet-like administration forms is explained in more detail below with reference to illustrative embodiments which follow. These involve a sequence of work steps, as follows:

Mass Production:

Individual components are brought together in a specific manner, dissolved and mixed. The solvent used is water or an ethanol/water mixture.

Coating:

Application device: rollers, coating box, nozzles continuous coating on: I. structured support (e.g. Teflon, special steel) II. dehesively treated material (e.g. paper or foil) with planar surface III. as under II Drying:

re I. By means of hot air.

re II. By means of hot air, with "warmer and colder" zones having to be provided. In this way, a foil-like band is obtained which has different thicknesses. At the warmer zones, the material is thicker, and at the colder zones it is thinner.

These zones are obtained by
  a) an open-worked surface, e.g. lattice hole structure of the band-shaped support,
  b) use of materials with different heat conduction in the production of the conveyor belt,
  c) dehesively treated material in which segments with differing heat conduction properties are implanted.

re III. By means of hot air as under I., and additional use of a structured embossing roller.

Fabrication:

1. Cutting lengthwise in narrow rolls.
2. Separating by punching or transverse cutting (in the case of II., the paper or the foil is first removed).
3. Packing.

Further details, features and advantages of the invention will be evident from the following explanation of two illustrative embodiments which are shown diagrammatically in the drawings, in which:

FIG. I is a diagrammatic representation, in cross section, with production of the coding on a support exhibiting thickness differences, FIG. II shows, in cross section, the production of a coding by means of subjecting the preparation to local temperature differences.

FIG. I shows the preparation (1) on a structured support (2) which has a sequence of elevations (3) and depressions (4). Correspondingly, depressions (13) develop reciprocally in the preparation (1) opposite the elevations (3), and elevations (14) develop opposite the depressions (4) within the preparation layer. Heat is delivered in a heat stream (9) which can involve both radiation and also convection.

FIG. II shows a manufacturing method in which the thickness differences (13, 14) in the layer (1) of the preparation are produced using local temperature differences during drying. Here, the preparation layer (1) lies on a foil-like carrier (5), for example silicone paper, aluminium foil, plastic foil or the like. A conveyor belt is designated by (6), which has a lattice or hole structure consisting of bridges (7) and openings (8). By means of heat delivered to the bridges in accordance with the arrows (10), these form warmer areas in contact with the carrier foil (5) and colder areas in the region of the openings (8). In the area of the warmer zones, the material turns out thicker on drying, while it is thinner in the colder areas. In this case, the drying can also be assisted from above, for example, likewise by a stream (9) of heated air. The temperature differences of the conveyor belt (6) can be generated, for example, by inductive heating of the bridges (7) of the lattice structure or by radiation or contact heating, while the openings (8), for example, are cooled by convection with air.

The invention is uncomplicated and optimally satisfies the object set out in the introduction.

What is claimed is:

1. A pharmaceutical preparation, consisting of a sheet, film or wafer-shaped administration form with a coding in the form of at least one of characters or graphic symbols or patterns for identifying the substances affecting at least one of the group of flavor, odor, therapeutic and curative substances which can be released therefrom during use, wherein the coding is formed by areas in the pharmaceutical preparation of differing thickness which are visible upon looking through the pharmaceutical preparation.

2. The pharmaceutical preparation of claim 1 wherein the areas of differing thickness in the pharmaceutical preparation have the same density.

3. The pharmaceutical preparation of claim 1 wherein the areas of differing thickness in the pharmaceutical preparation have a different density.

4. A method for producing the pharmaceutical preparation of claim 1 comprising forming the areas of differing thickness in the pharmaceutical preparation under the action of pressure.

5. A method for producing the pharmaceutical preparation of claim 1 comprising forming the areas of differing thickness in the pharmaceutical preparation without the action of pressure.

6. The method of claim 4 further comprising producing thickness differences in the areas in the pharmaceutical preparation by coating of a support which has a sequence of elevations or depressions corresponding to the coding.

7. The method of claim 5 further comprising producing thickness differences in the areas in the pharmaceutical preparation by coating of a support which has a sequence of elevations or depressions corresponding to the coding.

8. The method of claim 4 further comprising producing thickness differences in the areas in the pharmaceutical preparation by subjecting the pharmaceutical preparation to local temperature differences during drying.

9. The method of claim 5 further comprising producing thickness differences in the areas in the pharmaceutical preparation by subjecting the pharmaceutical preparation to local temperature differences during drying.

10. The method of claim 4 further comprising introducing symbols or patterns intermittently.

11. The method of claim 5 further comprising introducing symbols or patterns intermittently.

12. The method of claim 4 further comprising introducing symbols or patterns continuously.

13. The method of claim 5 further comprising introducing symbols or patterns continuously.

14. A method for producing the pharmaceutical preparation of claim 1 comprising coding of the areas of the pharmaceutical preparation while the pharmaceutical preparation is in a plastically deformable state.

15. The method of claim 4 further comprising producing thickness differences in the areas in the pharmaceutical preparation by coating of a support which has a sequence of elevations and depressions corresponding to the coding.

16. The method of claim 5 further comprising producing thickness differences in the areas in the pharmaceutical preparation by coating of a support which has a sequence of elevations and depressions corresponding to the coding.

* * * * *

UNITED STATES PATENT AND TRADEMARK OFFICE
CERTIFICATE OF CORRECTION

PATENT NO. : 6,106,930
DATED : Aug. 22, 2000
INVENTOR(S) : Ludwig

It is certified that error appears in the above-identified patent and that said Letters Patent is hereby corrected as shown below:

On cover page, at line [73], please delete "Isis Pharmaceuticals Inc., Carlsbad, Calif." and insert therefor --LTS Lohmann Therapie-Systeme GmbH, Neuwied, Germany--

On cover page, at line [*], please delete "Notice: This patent is subject to a terminal disclaimer"

Signed and Sealed this

Twenty-ninth Day of May, 2001

Attest:

NICHOLAS P. GODICI

Attesting Officer    Acting Director of the United States Patent and Trademark Office